United States Patent [19]

Razi

[11] Patent Number: 5,542,936
[45] Date of Patent: Aug. 6, 1996

[54] SHEATH FOR INTRODUCING CATHETER

[76] Inventor: Dean M. Razi, 4810 W. Gandy Blvd., Tampa, Fla. 33611

[21] Appl. No.: 406,587

[22] Filed: Mar. 20, 1995

[51] Int. Cl.$^6$ ............................................. A61M 5/00
[52] U.S. Cl. .......................... 604/264; 604/158; 604/171
[58] Field of Search ................................ 128/656–658, 128/772; 604/43, 93, 104–109, 171, 264, 268, 280, 158, 167; 606/108, 194, 198

[56]     References Cited

U.S. PATENT DOCUMENTS

| | | | |
|---|---|---|---|
| 3,877,429 | 4/1975 | Rasumoff | 606/108 X |
| 4,592,341 | 6/1986 | Omagari et al. | 606/108 X |
| 4,648,402 | 3/1987 | Santos | 606/198 |
| 4,705,041 | 11/1987 | Kim | 606/108 |
| 4,722,725 | 2/1988 | Sawyer et al. | 604/167 X |
| 4,883,474 | 11/1989 | Sheridan et al. | 606/108 X |
| 5,078,689 | 1/1992 | Keller | 604/167 |
| 5,129,910 | 7/1992 | Phan et al. | 606/108 X |
| 5,178,611 | 1/1993 | Rosenberg | 604/158 X |
| 5,188,619 | 2/1993 | Myers | 604/264 X |
| 5,207,684 | 5/1993 | Nobles | 606/108 |
| 5,250,038 | 10/1993 | Melker et al. | 604/167 X |
| 5,275,610 | 1/1994 | Eberbach | 606/198 |
| 5,304,119 | 4/1994 | Balaban et al. | 606/108 X |
| 5,320,610 | 6/1994 | Yoon | 604/158 |
| 5,387,196 | 2/1995 | Green et al. | 604/158 |
| 5,403,284 | 4/1995 | Gross | 604/167 |

*Primary Examiner*—Corrine M. McDermott
*Assistant Examiner*—N. Kent Gring
*Attorney, Agent, or Firm*—Dominik & Stein

[57]     ABSTRACT

An introducer sheath for inserting a catheter into a circulatory vessel, such as the femoral artery. The introducer sheath is in the form of a tube having an open proximal end, an open distal end, and a lumen through which a device such as a catheter can be passed. The introducer sheath is provided with at least one, preferably multiple, fenestration through the tube wall, preferably at the outer radius of curvature of the introducer sheath where the sheath bends to transition from lying parallel to the femoral artery to being at an angle so as to exit the femoral artery, tissue and skin, such that blood can flow through the introducer sheath and continue to the extremities after the introducer sheath is inserted.

6 Claims, 4 Drawing Sheets

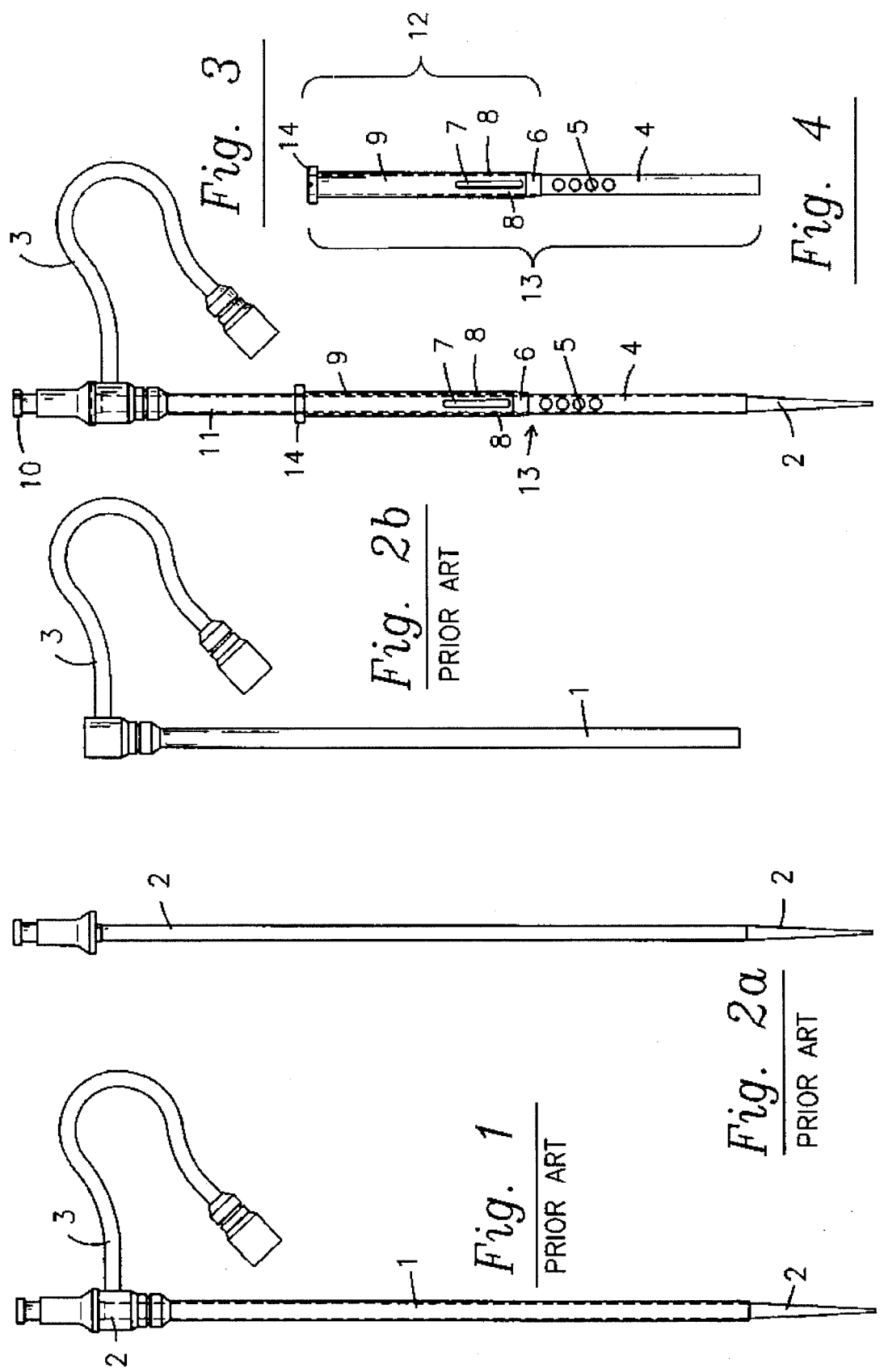

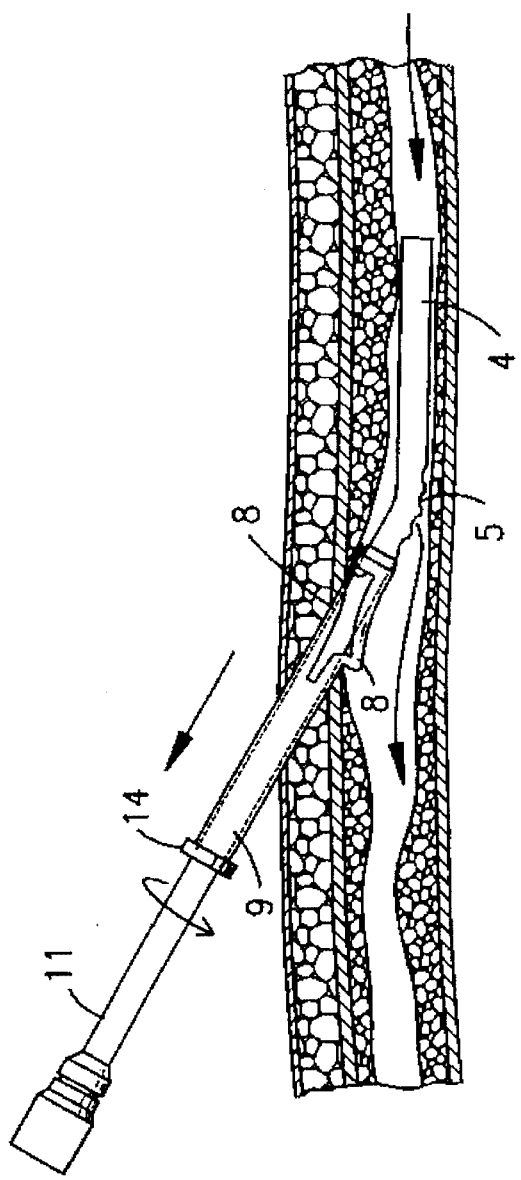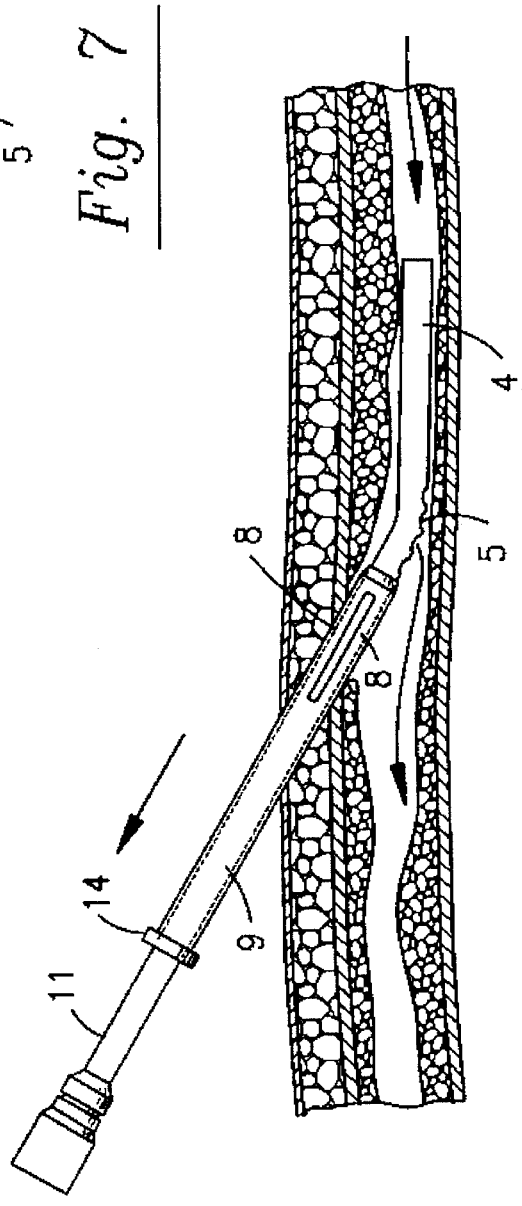

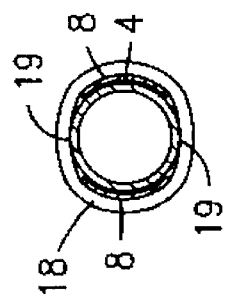
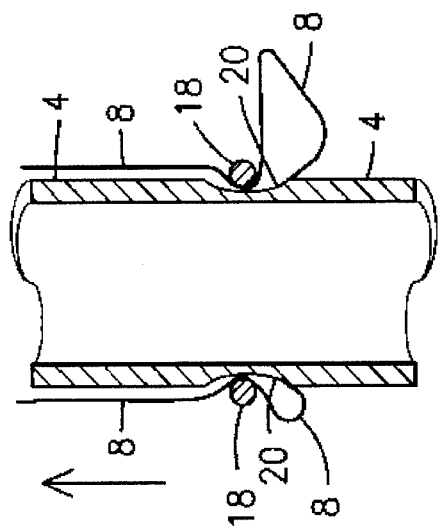
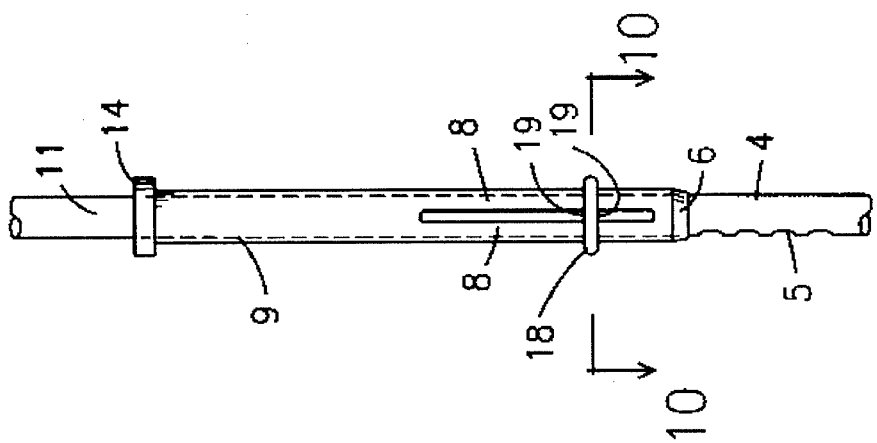
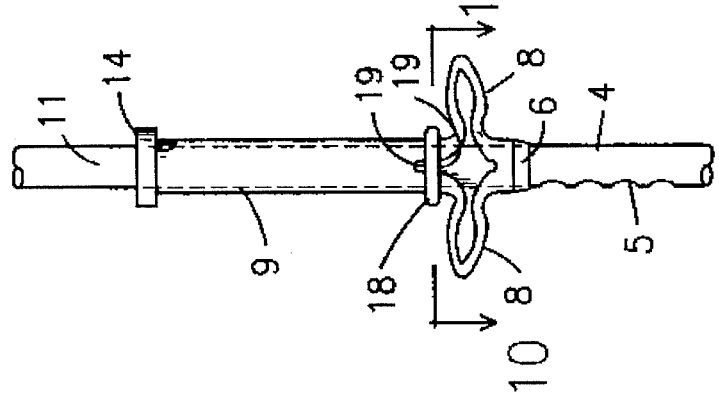

SHEATH FOR INTRODUCING CATHETER

BACKGROUND OF THE INVENTION

1. Field of the Invention

The invention concerns an introducer sheath for inserting a catheter into a circulatory vessel, such as the femoral artery. The introducer sheath prevents obstruction of the vessel and thus eliminates the risk of ischemia, tissue hypoxemia, and thrombosis. The invention further concerns a percutaneous method for inserting the introducer sheath, and a means by which the catheter can be securely anchored in the blood vessel so as its side holes not to move relative to the blood vessel's main lumen and the distal blood flow remains uninterrupted.

2. Description of the Related Art

The development of miniaturized surgical instruments and probes has resulted in an increase in the popularity of non-invasive surgery.

For example, percutaneous translumenal coronary angioplasty involves the percutaneous introduction of an inflatable balloon tipped catheter assembly into the femoral artery and its advancement, distally, through the arterial system to the situs of, e.g., an atherosclerotic lesion. The balloon is then inflated to dilate the constricted vessel.

Another surgical technique, intra-aortic balloon pump (IABP) counterpulsation, provides circulatory assistance to a patient experiencing a cardiogenic shock. Using a needle, a guide wire and a dilator sheath assembly, an elongated catheter-mounted balloon pump is inserted percutaneously through an introducer sheath into a femoral artery, and the assembly travels through the abdominal aorta towards the heart and is positioned into the descending thoracic aorta. After the pump is properly positioned in the thoracic aorta it is inflated and deflated phased with the patient's ECG in a manner to produce diastolic counterpulsation. The intra-aortic balloon thereby functions as a pump, assisting the flow of blood through the coronary and carotid arteries in diastole and to the body during balloon deflation.

Despite advances in non-invasive surgery, techniques such as intra-aortic balloon pump counterpulsation remain hazardous. The introducer sheath, through which the balloon tipped catheter must pass, obviously has a larger outer diameter than the outer diameter of the balloon tipped catheter. Particularly in females, which generally have smaller diameter arteries, and patients with peripheral vascular disease, these introducer sheaths can block blood flow, causing arterial thrombosis. Further, the devices may, in some instances, remain in the body for extended periods of time, i.e., several days or more. Special precautions must thus be taken to prevent the introducer sheath or guide cable from blocking or restricting blood flow through the femoral artery. Loss of blood flow to the lower extremities results at a minimum in ischemia and localized tissue anoxemia, and in severe cases can result in amputation of the patient's leg.

One prior art technique for reducing the risk of circulatory blockage involved the use of a double lumen catheter with an inner lumen for injection of dyes, monitoring blood pressure, etc, and with an outer crescent shaped outer lumen with one side hole, as disclosed in the U.S. Pat. No. 4,755,176. However, when using such a design the single side hole could be completely blocked and sealed by atheromatous plaques within the intima of the femoral artery, leading to thrombosis of the second or outer crescent shaped channel. Further, this teaching concerns a catheter and not an introducer sheath.

Yet a further problem with an emplaced introducer sheath is the tendency for the sheath to move relative to the blood vessel's main channel, diverting the fenestrations' blood streams to the sidewall of a small female gender type of artery such that the distal blood flow will be stopped.

While the above mentioned patents are representative of the designs which have been developed to provide catheters or introducer sheaths for introducing catheters into bodily vessels, each clearly has inherent problems, limitations and disadvantages.

SUMMARY OF THE INVENTION

An object of the present invention is to provide a catheter introducer device with which the degree of obstruction in the femoral artery, and thus the risk of non-invasive surgery, is lowered.

A further object of the invention is to provide a percutaneous method for inserting an improved introducer sheath such that the risk of obstruction of the femoral artery or other circulatory vessel is eliminated.

Yet a further object of the invention is to provide a means by which the catheter can be securely anchored in the blood vessel so as not to move relative to the blood vessel, and so that its side holes remains within the main channel of the vessel in order to provide distal blood flow.

These and other objects of the invention are accomplished by an introducer sheath for introducing a catheter or the like into a bodily passageway, the introducer sheath being in the form of a tube having an open proximal end, an open distal end, and a lumen through which a device such as a catheter can be passed. The introducer sheath is provided with at least one, preferably multiple, fenestration through the tube wall, preferably at the outer radius of curvature of the introducer sheath where the sheath bends to transition from lying parallel to the femoral artery to being at an angle so as to exit the femoral artery, tissue and skin.

The introducer sheath is preferably provided with a registration or marking so that the position of the fenestration can be readily determined. When the introducer sheath is properly placed in an artery, the fenestration eliminate the risk of blockage to blood flow, i.e., blood can flow down the descending aorta/the iliacs and femoral arteries, enter through the distal end of the introducer sheath, flow through the lumen of the introducer sheath, exit the introducer sheath through the fenestration, and continue on down the superficial and deep femoral arteries to perfuse the lower extremities.

In a further preferred embodiment of the invention, the introducer sheath is provided with flaps which can be caused to be deployed while the introducer is positioned inside the artery or other bodily passageway and serve as an anchor for preventing displacement of the introducer sheath side holes, and particularly preventing rotation of the side holes, and so prevents obstruction by plaques, yet these flaps make possible an easy removal of the introducer sheath from the artery or bodily passageway when its mission has been accomplished.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other introducer sheaths for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the present invention reference should be made the following detailed description taken in with the accompanying drawings in which:

FIG. 1 is a side view of a combination dilator and introducer sheath according to the prior art; FIG. 2a,b shows the dilator and introducer sheath according to FIG. 1, with the dilator and introducer sheath separated;

FIG. 3 shows a side view of a combination dilator and introducer sheath according to the present invention;

FIG. 4 shows the dilator and introducer sheath according to FIG. 4, with the dilator and introducer sheath separated;

FIG. 7 shows the introducer sheath in the process of removal, with the anchor flaps in the process of being retracted;

FIG. 8 shows the introducer sheath and about to be removed with anchor flaps fully retracted;

FIG. 9a shows a cross section of an embodiment of the introducer sheath with an additional ring-shaped member to permit retraction of the flaps with the inserter in place;

FIG. 9b shows a the introducer sheath of FIG. 9a with the flaps fully retracted;

FIG. 10 is a cross-section along line 10 of FIG. 9a; and

FIG. 11 is a sagittal view of a more preferred embodiment of the ring-configured introducer, showing the flap retrieval path.

DETAILED DESCRIPTION OF THE INVENTION

Figure 5:
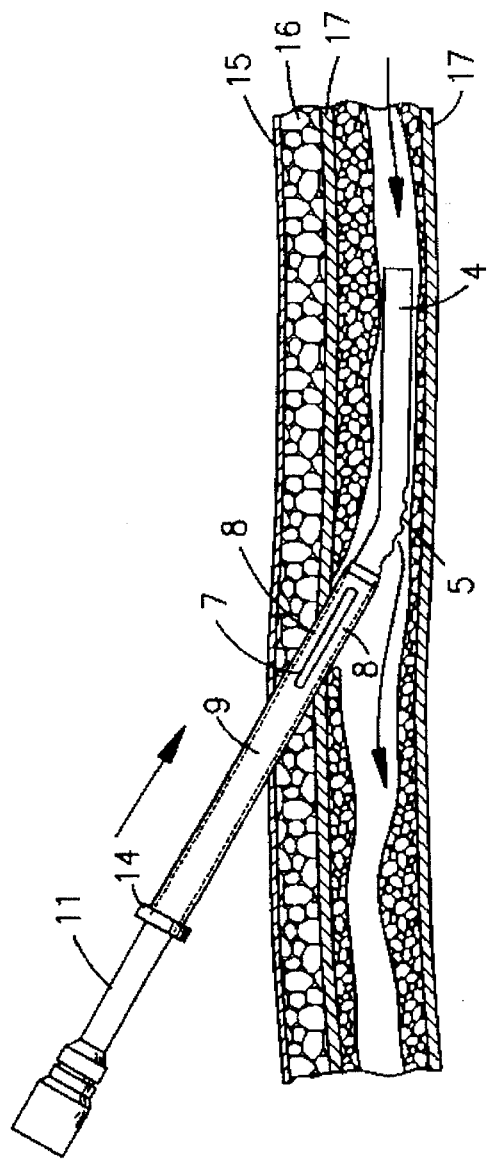
FIG. 5 shows the newly inserted introducer sheath in place prior to extending the anchor flaps.

The introducer sheath according to the present invention is a device for facilitating the access of a catheter, cannula, cable, etc., into a circulatory vessel or other bodily passageway, and is in no way limited to any specific device which can be introduced through the introducer sheath. The introducer sheath not only maintains an open passageway into the vessel, it also facilitates the transmission of pushing forces to the introduced catheter, cable, etc.

Devices which are introduced into the body and used to assist the pumping action of the heart are well known and need not be described in detail here. See, for example, U.S. Pat. Nos. 4,362,150, 5,120,299 and 5,230,692. Devices and procedures for balloon angioplasty are disclosed in, for example, U.S. Pat. Nos. 4,299,226, 5,007,898 and 5,338,296. The present invention concerns the introducer sheath for introducing any of the intravascular devices.

The introducer sheath is comprised of a biocompatable material such as a synthetic polymer. In a preferred embodiment, the introducer sheath is manufactured from a resilient plastic material such as polytetrafluoroethylene (Teflon®), polyethylene, polyurethane or nylon, and the anchor tube or flaps are manufactured from polyurethane.

The introducer sheath is in the form of a tube having an open proximal end, an open distal end, and a lumen through which the device, such as a catheter, can pass. The introducer sheath lumen is dimensioned to permit passage of a surgical device such as a balloon and its cable. Since the diameter of the catheter is smaller than the diameter of the balloon and thus the introducer sheath lumen, the catheter has a loose fit within the introducer sheath lumen, and this loose fit provides a passage for blood flow.

Fenestration are preferably at the outer radius of curvature of the introducer sheath where the sheath bends to transition from coaxial with the femoral artery to being at an angle so as to exit the femoral artery, tissue and skin. The shape and number of the fenestration is not particularly limited. Relatively circular fenestration are easily formed and do not present sharp corners or edges which may irritate or damage tissue. One fenestration may be enough to prevent occlusion and permit perfusion of the extremities; however, in order to insure that at least one properly positioned fenestration is present without requiring undue surgical care or attention, it is preferred to provide two or more, and preferably about four, fenestration. The fenestration are provided on at least one side (the downstream side) of the inserter sheath, but may be provided on more than one side.

The proximal end of the introducer sheath is preferably provided with a one-way valve, preventing flow of blood out the introducer.

The proximal end of the introducer sheath may be provided with or mated to a Y-coupling. Diluted heparin may be administered here to prevent thrombosis within the sheath.

The introducer sheath is blunt ended. The segment of the dilator which fits within the introducer sheath fits the internal diameter of the introducer sheath and is relatively constant in diameter. An approximately 2 cm segment of the dilator protrudes from the distal end of the introducer sheath and is tapered to facilitate entry of the introducer sheath into the artery. The dilator has its own internal channel which fits over the guide wire. After the dilator and introducer sheath are inserted, and the guide wire is inserted through the dilator, the dilator is removed and replaced by the balloon pump which is passed through the sheath.

To facilitate the understanding of the invention, the invention will now be explained using an intra-aortic balloon pump (IABP) assembly as a non-limiting example.

In order to use the IABP in the introducer sheath according to the invention, first the distance from the incision site to the target site is measured. A corresponding length of balloon-tipped catheter is measured and marked. This mark indicates the distance the balloon must be inserted into the femoral artery to reach the target site. Alternatively, a catheter having centemeter markings is used.

Next, a hypodermic needle is inserted into the femoral artery. A guide wire is inserted into the femoral artery through the hypodermic needle. The guide wire may be sufficient in length to reach the central arch (e.g. up to about 170–190 cm or longer). The needle is removed leaving the guide wire in place. The puncture hole created by the needle is then expanded by a dilator's distal segment (for example, an 8-French dilator) which slides over the guide wire allowing the dilator and introducer sheath assembly to be passed through the hole over the guide wire and into the femoral artery. The introducer sheath has an inside diameter generally corresponding to the outside diameter of the IAB to be inserted. The guide wire is removed and may be replaced by a second guide wire which is fed up through the artery to the vicinity of the aortic arch. The dilator is then removed. The IAB is passed over this second guide wire, if present, and slides up through the introducer sheath and along the artery to a point just below the aortic arch.

The introducer sheath is sutured to the skin. In one preferred embodiment of the invention, the introducer sheath is provided on each of its upper and lower surfaces with a four-panel flap. The first panel is the distal panel and is securely attached to the introducer sheath at a point which will be inside the bodily vessel when in use, but distal to the fenestration(s). The second panel is demarcated by a fold line along which the second panel can fold outwardly away from the surface of the introducer. The third panel is demarcated by a fold line along which it is biased to return to towards the introducer. The fourth panel is demarcated by a fold line bending the flap to run parallel to the introducer surface. The fourth panel is preferably elongated and extends outside the skin, and/or may be bonded to a tubular member immediately superior to the introducer sheath, or other means may be provided for transmitting pushing and pulling forces to the fourth panel. Once the introducer sheath and the first three panels of the flaps have been introduced into the artery, the fourth panel is pushed distally to cause outward folding of the second and third panels away from the surface of the introducer sheath. The thus formed projections serve as anchors to insure proper registry of the fenestration with the blood flow path, and to prevent dislocation or rotation of the introducer sheath and to ensure that the blood flow reaches the open channel of the femoral artery and not the artery's side walls.

The number of flaps may be one, two, or four or more. If only one flap is provided, it is preferably provided in the side of the vessel which has the greatest angle to the introducer sheath. That is, if only one anchor flap is used, it should be in the direction opposite of the direction of the introducer sheath insertion, so that it functions as an anchor preventing the malpositioning or malrotation of the sheath's side holes.

In a more eloquent and more preferred embodiment of the anchor mechanism, a thin-walled anchor tube is formed over the introducer sheath. The distal end of this anchor tube is fixed to the introducer sheath at a point adjacent to and proximal to the perfusion fenestration. Except for the fixed distal end, the anchor tube is snugly but slidably fitted over the introducer sheath. The fit should be snug to prevent any possibility of blood loss through the space between the introducer sheath and the anchor tube.

The anchor tube is preferably provided with two longitudinal slits, one on each side. The proximal end of the anchor tube is exposed even after the introducer sheath has been planted in the operating position and can be manipulated by hand. The proximal end of the anchor tube is preferably provided with a flange or other protrusion to facilitate easier manipulation by hand of the exposed end of the anchor tube. To deploy the anchor flaps of the anchor tube, the introducer sheath is first slid back into the femoral artery slightly more than necessary, and the proximal end of the anchor tube is then urged distally while the introducer sheath is held in place. This movement of the proximal end of the anchor tube relative to the fixed distal end generates compression forces which cause the anchor tube to buckle outwards, forcing the two strips of the anchor tube, which strips are defined by the lateral slots in the anchor tube, to bulge outwards. The thus compressed anchor tube is fixed in the compressed relationship by, e.g., slightly rotating the flanged proximal end of the anchor tube to cause engagement with a locking mechanism pre-engineered into the introducer sheath. These outward bulging flaps of the anchor tube serve as anchors preventing the dislodging of the introducer sheath.

The lateral slots near the distal end of the anchor tube may be straight, or may be somewhat helical so that twisting of the proximal flange relative to the distal end of the anchor tube to cause locking of the proximal end of the anchor tube simultaneously causes a straightening of the protruding anchor tube flaps. Preferably, the lateral slots are straight along a longitudinal axis, and the locking mechanism is so designed that rotation away from the rest orientation of the proximal end flange of the anchor tube comprises an unlocked position, and returning the flange to the rest orientation results in locking. In this preferred embodiment, the locking of the flanged end of the anchor tube to the introducer sheath in the compressed state results in straight, non-twisting protrusions of the anchor flaps.

Once the introducer sheath is in place, the tip of the balloon tipped catheter is introduced into the femoral artery until it reaches the descending thoracic aorta, as indicated by the mark. The balloon is caused to inflate, preferably at the dicrotic notch of the arterial pressure, and to deflate, preferably just before isometric left ventricular contraction, thereby assisting the pumping function and improving circulation.

The design and function of the introducer sheath of the present invention will now be described with reference to the figures.

Referring first to FIG. 1, there is shown a prior art introducer 1 with dilator 2 within it and side port 3 attached via Y-adaptor.

FIG. 2a shows a conventional dilator 2 and FIG. 2b shows a conventional introducer 1.

FIG. 3, shows an introducer with upper segment 11 and lower segment 4 provided with fenestrations 5 according to a preferred embodiment of the present invention, with secondary hose 3 attached via Y-adaptor. Within the introducer sheath is dilator 2. Anchor tube 12 fits snugly but slidably over introducer sheath 13. Longitudinal slits 7 (only one of which is shown) in the anchor tube separate two anchor flaps 8. The lower or distal end 6 of anchor tube 12 is fixed to introducer sheath 13. Upper segment 9 of the anchor tube 12 is free to slide over the introducer sheath 13, and can be operated by hand by manipulating flange 14.

FIG. 5 shows the introducer sheath in place in the atheromatous femoral artery 17 below skin 15 and subcutaneous fatty adipose tissue 16. Blood flowing in the direction shown in the artery flows into the lumen of introducer sheath 4 and out fenestration 5. Since the outer diameter of a catheter or cable (not shown) is smaller than the inner diameter of the introducer sheath, a catheter or cable passing through introducer sheath 4 does not occlude the flow of blood.

Figure 6:
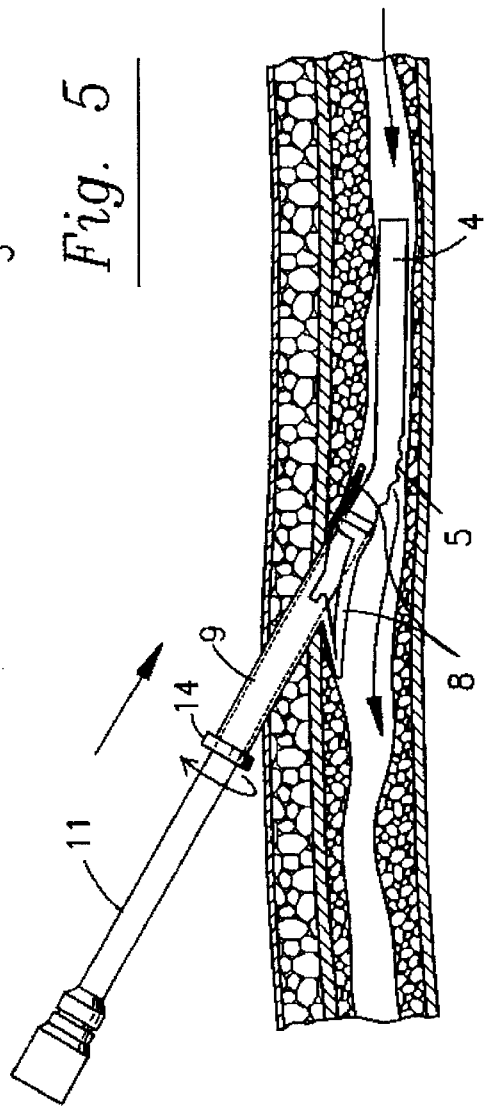
FIG. 6 shows the introducer sheath in place subsequent to extending the anchor flaps.

FIG. 6 shows the downward or distal movement of the slidable portion of the anchor tube 9 and locking in place of flange 14. This compression of the anchor tube causes anchor flaps 8 to bulge out into the femoral artery and thereby to serve as anchors. Once the anchor flaps 8 are deployed, the inserter sheath can be withdrawn to the point where the anchor flaps securely contact the upper wall of the femoral artery. At this time, the introducer sheath is ready for the insertion of the intra-aortic balloon pump.

In order to facilitate the withdrawal of tube 9, the introducer sheath 4 is preferably first urged further into the femoral artery. FIG. 7 shows the unlocking of flange 14 and withdrawal of anchor tube 9 while leaving introducer sheath 4 in place. This relative movement of the anchor tube removes the compressive forces acting on anchor flaps 8, collapsing the flaps against the introducer sheath 4 as shown in FIG. 8. Once the anchor flaps 8 are flush against the introducer shaft 9, the introducer sheath assembly can be withdrawn.

The present inventor has further considered that some cardiologist may prefer an introducer sheath assembly which does not require pushing the sheath back into the artery and pulling on the hub at the same time while withdrawing the assembly at the termination of the procedure, considering the reintroduction of the exposed segment of the anchor tube to increase the theoretical chance of infection (a chance which, however, is remote because of the presence of another soft wrapping latex which covers over the entire cutaneous part of the unit and which allows the manufacture of the parts without touching the unit itself). In consideration thereof, the present inventor has developed yet a further preferred introducer sheath with additional optional components.

As shown in FIG. 9a, the additional optional components consist of a traverse loop or ring 18 which is fused 19 to the introducer sheath 4 in the area of the slit between the flaps 8, or D-rings, strips of material, etc. This ring fits only over the most distal part of each fourth panels immediately adjacent the fold line of the fourth-to-third panel when the anchor flaps are fully deployed. These loops, strips, etc. form "bridges" over the flaps. To retract the flaps, the fourth panels or anchor tubes 9 are pulled lateral proximally. The third and then second panels of the flap pass under the bridge and are straightened out by the bridge inside the lumen of the vessel as seen in FIG. 9b, so that they are withdrawn proximally closely adjacent to the proximal introducer sheath surface 11. Since the flaps 8 are being pulled out close to the inserter sheath, there is no concern that the withdrawing flaps may engage with and damage the vessel wall, subcutaneous tissue or skin. This is similar to pulling an end of a bow-tie to untie it see (FIG. 11). Accordingly, there is no need to push the inserter sheath into the vessel prior to withdrawing it, as was necessary in the case that no ring 18 is provided.

FIG. 11 shows an even more preferred embodiment of the invention, where inserter sheath 4 is provided with recesses 20 so that ring 18 substantially does not protrude from, and increase the outer diameter of, the introducer sheath. The right side of FIG. 11 shows flap 8 in the deployed position. The left side of FIG. 11 shows flap 8 being withdrawn by being pulled in the direction shown by the arrow, such that flap 8 must pass between ring 18 and introducer sheath 4.

The ring 18 may have rounded edges, may have right-angled edges, may have beveled edges, and preferably has tapered edges giving a generally triangular profile so as to facilitate insertion and withdrawal through the skin puncture.

In the embodiments shown in FIGS. 9–11, the introducer sheath is provided with the flaps in the deployed position. The sheath is introduced into the bodily vessel with the flaps in the deployed position. Thus, there is no requirement that the anchor tube and flaps be constructed with sufficient rigidity to be capable of being deployed after introduction of the inserter sheath into the vessel. All that is necessary is that means be provided capable of pulling the deployed flaps under the ring 18 until the flaps are flat against the sides of the introducer sheath as shown in FIG. 9b. This means for pulling the deployed flaps may be thin strips of cellophane, thread, plastic, etc.

In yet a further preferred embodiment of the invention, the flaps are not operated by means of a sliding anchor tube, nor is a ring provided for their retraction. In this further preferred embodiment, the second and third flaps are folded out in the deployed state and temporarily bonded together by means such as a waxy material, a pressure sensitive adhesive, or they may even be unitized and held together by a partially perforated seam or any other means which permits them to be easily separated from each other. Such a construction allows the four panels, or corresponding elements, to take the shape of deployed flaps and to be inserted through the skin, tissue and lumen into the aorta in the deployed condition. Once the introducer sheath is ready to be removed, all that is necessary is that the fourth panel or thread or cellophane strip or other element attached to the third panel be pulled to undo the flaps, thus removing the anchor feature and enabling retraction of the introducer sheath.

In yet a further embodiment of the invention, the anchor flaps are attached to the introducer sheath by means of a partially perforated membrane, adhesive, etc. which means insure that the flaps remain attached to the introducer sheath while the introducer sheath is in use in the body. When removal of the introducer sheath is indicated, elements attached to the flaps, such as threads or cellophane strands are pulled, detaching the flaps from the introducer sheath.

The above has described only a few of the myriad of ways in which anchor flaps can be attached, deployed, and retracted.

Although the system was first designed as a device for facilitating introduction of intra-aortic balloon pump, it will be readily apparent that the combination is capable of other uses, and is not specifically limited to use in conjunction with the circulatory system. Although this invention has been described in its preferred form with a certain degree of particularity with respect to introduction of an intra-aortic balloon pump, it is understood that the present disclosure of the preferred form has been made only by way of example and that numerous changes in the details of structures and the composition of the system may be resorted to without departing from the spirit and scope of the invention.

Now that the invention has been described,
What is claimed is:

1. An introducer sheath for introducing a catheter into a bodily passageway, the introducer sheath being tubular and having an open proximal end, an open distal end, and defining a lumen through which a catheter can be passed, said introducer sheath being provided with at least one fenestration wherein when said distal end of said tubular introducer sheath is inserted into a bodily passageway through a surgical opening the distal end is oriented coaxial with the bodily passageway, the proximal end is oriented coaxial with the surgical opening, and said introducer sheath describes an arc in the area in which it transitions from the orientation of the axis of insertion to the orientation of the axis of the bodily passageway, wherein said at least one fenestration is located at the outer radius of curvature of the introducer sheath at said arc, and wherein said introducer sheath is further comprised of an anchor tube having an inner diameter dimensioned for sliding over said introducer sheath, said anchor tube having a proximal end and a distal end and fixed at said distal end to said introducer sheath proximally to said fenestration, a segment of said anchor tube provided with at least two longitudinal slits for separating said anchor tube into at least two strips of material, such that urging of said slidable end towards said fixed end causes said strips of material to bulge outwardly.

2. An introducer sheath as in claim 1, wherein said anchor tube is comprised of polyurethane.

3. An introducer sheath as in claim 1, wherein said fixed end of said anchor tube is fixed immediately adjacent said at least one fenestration.

4. An introducer sheath as in claim 1, wherein said proximal end of said anchor tube is provided with a flange capable of being grasped by hand, and wherein said slidable end of said anchor tube is provided with means for locking engagement with said introducer sheath when said strips of material are in the state of bulging outwardly.

5. An introducer sheath for introducing a catheter into a bodily passageway, the introducer sheath being tubular and having an open proximal end, an open distal end, and a lumen through which a catheter can be passed, wherein said introducer sheath is provided with at least one fenestration through the sheath at a position such that said fenestration is within the bodily passageway when in use, wherein bodily fluids can flow into said open distal end of the introducer sheath and out said at least one fenestration, said introducer sheath further comprising:

at least one bridge member extending over and spaced apart from said introducer sheath and forming an aperture; and at least one strip of material having a proximal end and a distal end and attached at said distal end to said introducer sheath immediately adjacent to and distal from said bridge member and passing under said bridge member, said strip of material capable of sliding under said bridge member;

wherein strip material distal of said bridge member forms a fold, and wherein said fold can be withdrawn by proximal pulling of the proximal end of said strip of material.

6. An introducer sheath for introducing a catheter into a bodily passageway, the introducer sheath being tubular and having an open proximal end, an open distal end, and a lumen through which a catheter can be passed, wherein said introducer sheath is provided with at least one fenestration through the sheath at a position such that said fenestration is within the bodily passageway when in use, wherein bodily fluids can flow into said open distal end of the introducer sheath and out said at least one fenestration, said introducer sheath further comprising:

at least one strip of material having a proximal end and a distal end, said distal end of said strip of material attached to said introducer sheath, said strip of material folded upon itself to form a releasable flap, and wherein pulling on said proximal end of said strip of material causes said flap to release from each other.

* * * * *